US010765346B1

(12) United States Patent
McLaughlin

(10) Patent No.: US 10,765,346 B1
(45) Date of Patent: Sep. 8, 2020

(54) METHOD OF CAPTURING A NON-DISTORTED IMAGE OF THE FOOT

(71) Applicant: Brendan Lee Adams McLaughlin, Menlo Park, CA (US)

(72) Inventor: Brendan Lee Adams McLaughlin, Menlo Park, CA (US)

(*) Notice: Subject to any disclaimer, the term of this patent is extended or adjusted under 35 U.S.C. 154(b) by 0 days.

(21) Appl. No.: 16/408,353

(22) Filed: May 9, 2019

(51) Int. Cl.
A61B 5/107 (2006.01)
A43D 1/02 (2006.01)
A43B 7/14 (2006.01)
A61F 5/14 (2006.01)
A61F 5/01 (2006.01)
G05B 19/4099 (2006.01)

(52) U.S. Cl.
CPC .......... *A61B 5/1074* (2013.01); *A43B 7/1465* (2013.01); *A43D 1/025* (2013.01); *A61F 5/0111* (2013.01); *A61F 5/14* (2013.01); *G05B 19/4099* (2013.01); *A43D 2200/60* (2013.01); *G06T 2207/10028* (2013.01); *G06T 2207/30244* (2013.01)

(58) Field of Classification Search
CPC ...... A43D 1/02; A43D 1/025; A43D 2200/60; G05B 19/4099; G05B 2219/45243; A43B 7/1465; A43B 5/12; A43B 7/145; A61B 5/1074; G06T 2207/10028; G06T 2207/30244; A61F 5/14; A61F 5/011; A61F 5/0127; A61F 5/019
See application file for complete search history.

(56) References Cited

U.S. PATENT DOCUMENTS

| 5,740,618 | A  | * | 4/1998  | Minden ............... A43B 5/12 36/71 |
| 6,954,557 | B2 | * | 10/2005 | Kim ................... A61B 5/0064 356/600 |
| 7,557,966 | B2 | * | 7/2009  | Pishdadian ......... A43D 1/025 358/474 |
| 7,706,028 | B2 | * | 4/2010  | Pishdadian ......... G01B 11/24 358/474 |
| 7,738,145 | B2 | * | 6/2010  | Pishdadian ......... G01B 11/24 358/474 |
| 7,978,378 | B2 | * | 7/2011  | Pishdadian ......... G01B 11/24 358/474 |
| 9,314,068 | B2 | * | 4/2016  | Schmutte ............ A43B 5/12 |
| 9,449,141 | B2 | * | 9/2016  | Schouwenburg ...... G16B 5/00 |
| 9,760,674 | B2 | * | 9/2017  | Schouwenburg ...... G16B 5/00 |
| 9,892,228 | B2 | * | 2/2018  | Schouwenburg ...... G16B 5/00 |

(Continued)

OTHER PUBLICATIONS

Scott, Clare; "3D Printed Ballet Shoes Offer Dancers Support and Protection from Injury"; 3Dprint.com; Aug. 10, 2018; https://3dprint.com/222120/3d-printed-ballet-shoes/ (Year: 2018).*

(Continued)

*Primary Examiner* — John Villecco

(57) ABSTRACT

The ability to capture an undistorted image of the foot or foot and ankle is essential to the production of effective custom orthotics and shoes. This patent solves the problem of providing an accurate three-dimensional measurement of an undistorted foot/ankle by using a system involving the automated and controlled orbit of a point cloud capture device around the foot/ankle with the foot/ankle in a non-weight bearing position so as to capture a three-dimensional image.

2 Claims, 3 Drawing Sheets

(56) References Cited

U.S. PATENT DOCUMENTS

| | | | |
|---|---|---|---|
| 10,013,803 B2* | 7/2018 | Mach Shepherd | G06T 17/20 |
| 10,496,786 B2* | 12/2019 | Schouwenburg | B33Y 50/00 |
| 2002/0048392 A1* | 4/2002 | Kim | A61B 5/0064 |
| | | | 382/128 |
| 2005/0022421 A1* | 2/2005 | Bruckner | A43B 5/12 |
| | | | 36/8.3 |
| 2014/0164169 A1* | 6/2014 | Rusu | G06Q 30/0621 |
| | | | 705/26.5 |
| 2014/0276094 A1* | 9/2014 | Lidtke | A61B 5/1079 |
| | | | 600/476 |
| 2015/0032242 A1* | 1/2015 | Schouwenburg | G16B 5/00 |
| | | | 700/98 |
| 2015/0210015 A1* | 7/2015 | Schouwenburg | G16B 5/00 |
| | | | 700/98 |
| 2016/0072986 A1* | 3/2016 | Jones | H04N 5/2252 |
| | | | 348/77 |
| 2016/0085907 A1* | 3/2016 | Schouwenburg | G16B 5/00 |
| | | | 700/98 |
| 2016/0101571 A1* | 4/2016 | Schouwenburg | B33Y 80/00 |
| | | | 602/5 |
| 2016/0101572 A1* | 4/2016 | Schouwenburg | B33Y 80/00 |
| | | | 602/5 |
| 2016/0107391 A1* | 4/2016 | Parish | B33Y 80/00 |
| | | | 700/98 |
| 2016/0110479 A1* | 4/2016 | Li | A43B 7/141 |
| 2017/0272728 A1* | 9/2017 | Rafii | H04N 13/239 |
| 2018/0160777 A1* | 6/2018 | Hei | G06Q 30/06 |
| 2018/0256112 A1* | 9/2018 | Cabal Mirabal | A61B 90/14 |
| 2018/0300445 A1* | 10/2018 | Schouwenburg | G16B 5/00 |
| 2019/0174874 A1* | 6/2019 | Lee | A43D 1/025 |
| 2019/0191823 A1* | 6/2019 | Kasuya | A43D 1/02 |
| 2019/0223763 A1* | 7/2019 | Schwartz | A61B 5/1036 |
| 2019/0269199 A1* | 9/2019 | Freed | A43B 5/12 |
| 2020/0000180 A1* | 1/2020 | Sherrah | A43D 1/025 |
| 2020/0037709 A1* | 2/2020 | Lahajnar | A43D 1/025 |

OTHER PUBLICATIONS

De Klee, Katie; "P-rouette is a 3D-printed ballet shoe designed to reduce pain"; Braceworks; Aug. 10, 2018; https://braceworks.ca/2018/08/14/health-tech/p-rouette-is-a-3d-printed-ballet-shoe-designed-to-reduce-pain/ (Year: 2018).*

* cited by examiner

METHOD OF CAPTURING A NON-DISTORTED IMAGE OF THE FOOT

FIELD OF INVENTION

The present invention is a method of capturing a three-dimensional image of the foot/ankle for use in fields such as preventive health, medical treatment, orthopedics, podiatrics, dance, and athletics.

BACKGROUND OF THE INVENTION

Typical foot orthotic fabrication methods involve making an impression of one's foot into a mold or cast by a professionally trained podiatrist. The podiatrist must physically examine the patient's foot, and place the foot in the mold, typically while standing. The impression is then manipulated and corrected in order to provide an orthotic that realigns one's foot. The impression of the foot in the mold or cast is then turned into an orthotic comprised of select materials using a milling machine. While this method, along with other existing methods, may be effective for some, they can be inaccurate in multiple disciplines. While the podiatrist is holding and bending the patient's foot into a corrected position (when necessary), the foot is tense, and thus highly susceptible to movement, causing the mold to be an inaccurate representation of the foot. If the impression in the mold is simply made without manipulation but in the standing position, the resulting impression of the foot is fundamentally inaccurate because the placing of the foot into a mold under weight-bearing conditions compresses the fat pads in the plantar surface of the foot and causes the lateral and medial arches of the foot to be stretched out of natural position. Considering that arch support is necessary for nearly all people, the disturbance of the shape of the arch of one's foot when placed in a weight-bearing condition (the mold), defeats the purpose of an arch-supporting custom orthotic. In addition to the mold-making method, some orthotics are made by use of a three-dimensional scanner wherein the patient places his or her foot on the transparent surface of a scanner in a semi-weight bearing condition. This method also produces an inaccurate measurement of the foot because the semi-weight bearing condition distorts the natural shape of the foot.

Furthermore, the basic method of making custom orthotics from a mold is expensive because it requires a professionally trained podiatrist to hold the foot in position during the mold. Medical insurance does not cover these causes in the absence of severe deformity or injury, and thus early use of customized orthotics for preventive health is not common due to the prohibitive cost. Additionally, the mold must be renewed for each patient, adding to the total cost of the orthotic. Lastly, the process is time-consuming, accounting for the examination of the patient's feet, the molding or casting, the manipulation of the mold or cast, and the development of the orthotic based on a negative impression of the mold.

The existing mold-making and three-dimensional scan methods of producing custom orthotics are also limited in the range of topography captured. Typically, these methods are only capable of capturing the plantar side of the foot, limiting the orthotic potential and range of use in different types of shoes and scenarios. Some types of specialized shoes, including medical and athletic shoes, such as ice skates, ski boots, and ballet shoes require customization of more than the planar aspect of the foot for optimization of the desired effect.

BRIEF SUMMARY OF THE INVENTION

The present invention is a system of capturing an accurate three-dimensional measurement of an undistorted foot and ankle through the use of the automated and controlled orbit of a point cloud capture device around the foot. This can be accomplished using either a point cloud capture device, photogrammetry, photogrammetric processing, or other technologies that create three-dimensional measurements. The digital image can then be manipulated via CAD to optimize fit or attain a therapeutic goal.

DETAILED DESCRIPTION OF THE INVENTION

Figure 1:
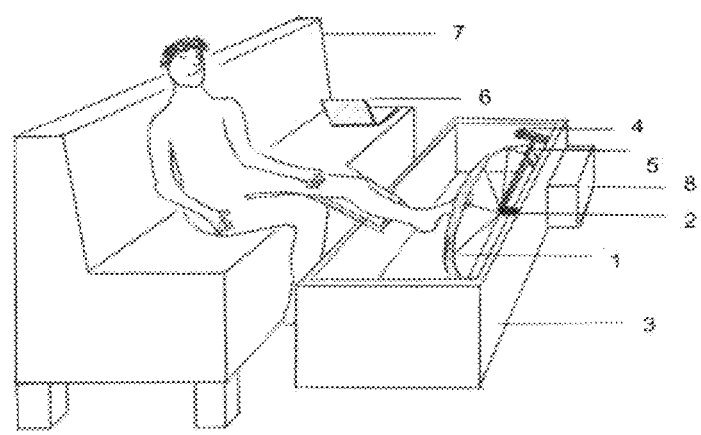
FIG. 1. System for capturing a non-distorted image of the foot containing a bench on which a patient sits (7), a rectangular prism-shaped support frame into which their patient extends their foot (3), a wheel attached to the support frame (1), a point cloud capture device (4), a support bar which connects the wheel and point cloud capture device (5), a stepper motor to simulate the rotation of the wheel (2), a small single-board computer to control the stepper motor (8), and a laptop computer to save the image captured (6).
Figure 1:
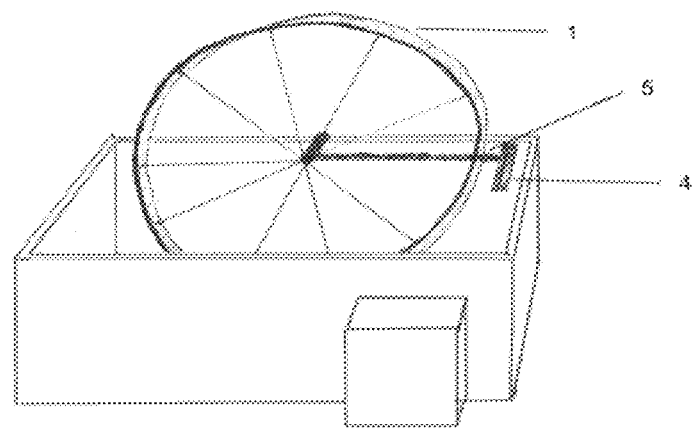
Figure 2:
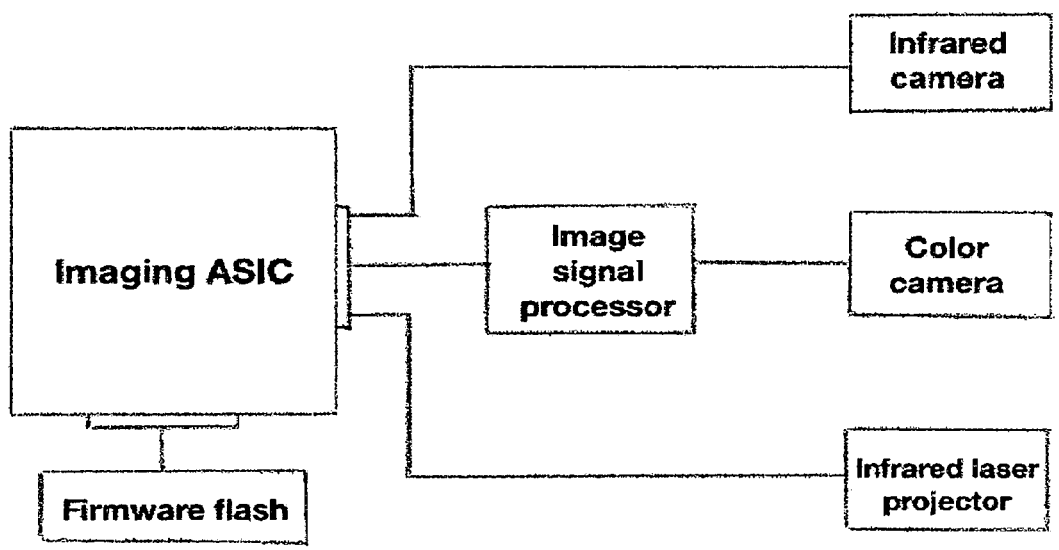
FIG. 2. Example of point cloud capture device.
Figure 3:
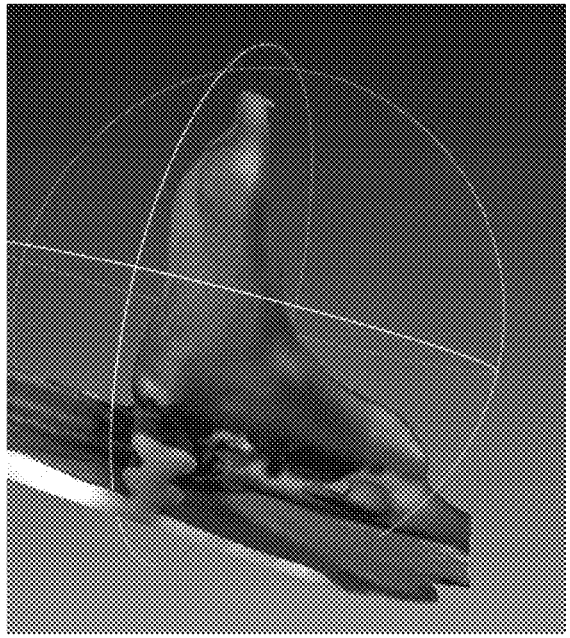
FIG. 3. A three-dimensional image taken of a foot using the system depicted in FIG. 1. Three views of the same object file are presented.
Figure 3:
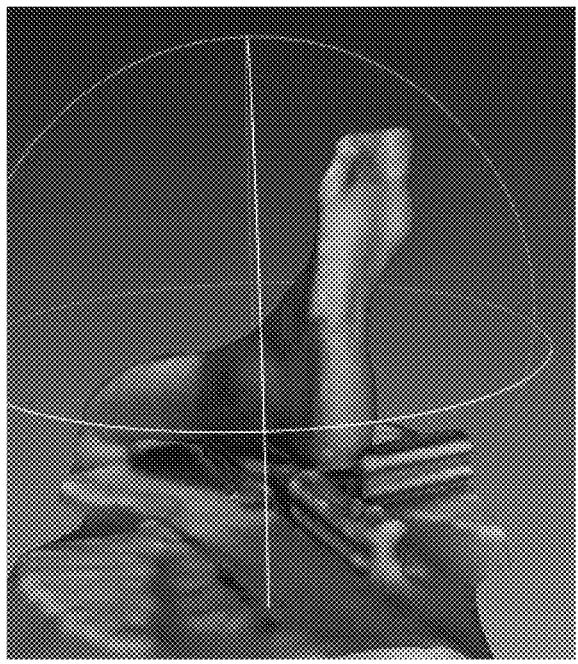
Figure 3:
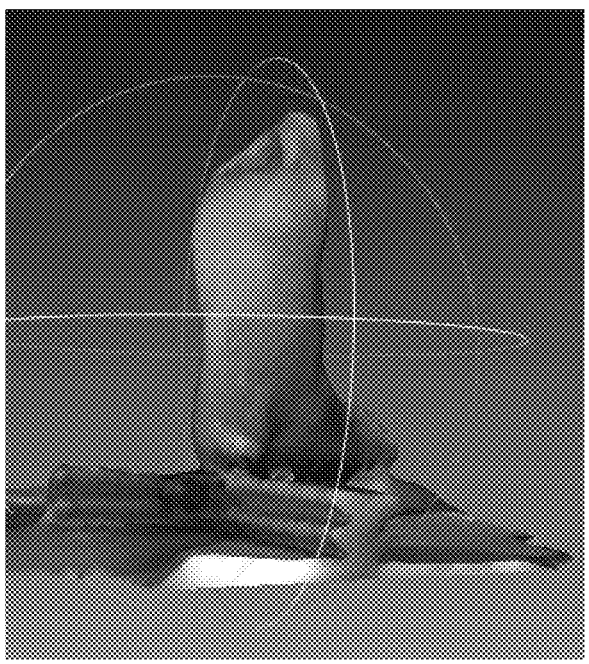

As depicted in FIG. 1, the foot must be suspended in a non-weight bearing position in which the foot is relaxed and still. This position can be achieved by having the patient sit in a chair that is tall enough to elevate the foot at least two feet off the ground, or the patient can sit in B a chair with their leg elevated by a calf support. Attached to a wheel, the point cloud capture device is secured at an ideal focal radius, as indicated by the device, away from the foot. The device must then be orbited around the foot in the shape of a semicircle from the lateral ankle to the plantar foot region to the medial ankle of the same foot. This orbit is automated by a single board computer that is connected to a stepper motor. The stepper motor is in contact with a rubber band that is wrapped around the circumference of the wheel. As the motor rotates, it rotates the rubber band which spins the wheel. Once the orbit of the point cloud capture device has completed its path from the lateral ankle to the medial ankle of the foot, the rotation of the stepper motor is terminated and the scan taken by the point cloud capture device is saved to a laptop.

An alternative method for capturing a non-distorted image of the foot and ankle is photogrammetry. In this method, a camera is used to take 50-100 photos of a patient's foot and ankle region from multiple angles. Acceptable cameras include smartphone cameras and compact cameras. The foot must be suspended in a non-weight bearing position in which the foot is relaxed and still as described above. Each photo must be taken from a different position and angle in order to capture the whole foot and ankle region. These photos are then uploaded to a photogrammetry software in which a three-dimensional object file is created.

For specialized images for which a non-relaxed position is desired, such as for the creation of toe and foot orthotics for ballet pointe shoes, the foot may be held in the desired position (for example, in the pointed position that would be used when the ballet dancer is on pointe). An image for this specific instance can be created by rotating a point cloud capture device from the dorsal aspect of the foot around the toes to the planter aspect of the foot. Meanwhile, the patient must be sitting on a bench or chair in the position described above with his or her foot held in the desired pointe position.

What is claimed is:

1. A system of capturing a three-dimensional measurement of an undistorted foot and ankle, the system comprising: a bench or chair on which a patient sits, wherein a point cloud capture device is rotated around the patient's foot in the shape of a semicircle from the lateral ankle to the plantar foot region to the medial ankle of the same foot, wherein the point cloud capture device is attached to a wheel, with a diameter between two and three feet, that is attached to and stabilized by a support frame, wherein the wheel is rotated by a stepper motor which rotates a rubber band that is wrapped around the wheel, wherein the stepper motor's motion is controlled by a computer.

2. The system of claim 1 wherein the point cloud capture device is integrated into a mobile phone.

* * * * *